US005785972A

United States Patent [19]
Tyler

[11] Patent Number: 5,785,972
[45] Date of Patent: Jul. 28, 1998

[54] COLLOIDAL SILVER, HONEY, AND HELICHRYSUM OIL ANTISEPTIC COMPOSITION AND METHOD OF APPLICATION

[76] Inventor: Kathleen A. Tyler, Route 5, Box 5285, Hermiston, Oreg. 97838

[21] Appl. No.: 781,460

[22] Filed: Jan. 10, 1997

[51] Int. Cl.$^6$ .............. A61K 35/78; A61K 35/64; A61K 33/38; A61K 31/685

[52] U.S. Cl. .............. 424/195.1; 424/539; 424/618; 514/78

[58] Field of Search .............. 424/195.1, 539, 424/618; 514/78

[56] References Cited

U.S. PATENT DOCUMENTS

| | | | |
|---|---|---|---|
| 3,761,590 | 9/1973 | Fox | 514/157 |
| 4,551,139 | 11/1985 | Plaas | 604/290 |
| 4,670,272 | 6/1987 | Chen et al. | 426/94 |

OTHER PUBLICATIONS

WE Lockhart MD; Early Treatment of Burns by Open Nitrate Spray; Rhode Island Medical Journal; Sep. 1977; 423–6.

Brentano MD, Margraf, Manafo MD & Moyer MD; Antibacterial Efficacy of a Colloidal Silver Complex; vol. 17, 1966, pp. 76–78.

Margraf & Moyer MD; Colloidal Silver; 1994; pp. 17, 20, 21 and 29–31.

Worwood; Complete Book of Essential Oils & Aromatherapy 1991; pp. 9, 400.

Lavabre; 1990; Aromatherapy Workbook; pp. 16, 36, 58, 60.

Mailhebiau; 1995; Portraits in Oils, p. 65.

Igram; A disaster Survival Guide; 1992; p. 26.

McDowell; Scientific American; Dec. 1996; p. 102.

Lawless, The Illustrated Encyclopedia of Essential Oils: The Complete Guide to the Use of Oils in Aromatherapy and Herbalism, Barnes and Noble, Inc., Element Books Ltd., p. 148, 1995.

Lu, Chinese System of Food Cures: Prevention and Remedies, Sterling Publishing Co., Inc., NY, pp. 130 and 132, 1986.

*Primary Examiner*—David M. Naff
*Assistant Examiner*—Janet M. Kerr
*Attorney, Agent, or Firm*—Floyd E. Ivey

[57] ABSTRACT

A composition of matter comprising a therapeutically active compound with antiseptic and osmotic characteristics for treatment or therapy for burns and open wounds experienced by animals and man and in particular to the treatment of thermal burns on humans by use of spray, mist, dropper or saturated bandage application of the solution disclosed. The compound in solution form composed of colloidal silver, helichrysum angustifolium or helichrysum italicum oil and raw honey emulsified with water soluble lecithin by agitation.

13 Claims, 1 Drawing Sheet

5,785,972

COLLOIDAL SILVER, HONEY, AND HELICHRYSUM OIL ANTISEPTIC COMPOSITION AND METHOD OF APPLICATION

FIELD OF THE INVENTION

The present invention relates generally to a composition of matter comprising a therapeutically active compound with antiseptic, osmotic and other characteristics, the process of preparing the compound in solution form and the process of application for treatment or therapy for burns and open wounds experienced by animals and man and in particular to the treatment of thermal burns on humans by use of spray, mist, dropper or saturated bandage application of the solution disclosed. This application principally discloses the compound comprising colloidal silver, Helichrysum angustifolium or helichrysum italicum oil and raw honey emulsified with water soluble lecithin by agitation, the process of preparing the compound and the process of application primarily by spray or mist for the treatment of burn and open wounds in animals and man.

BACKGROUND OF THE INVENTION

Silver complex compounds and colloidal silver are known in the prior art for use as therapeutic and antibacterial treatment of wounds experienced by humans primarily by thermal injury. Colloidal Silver, earlier used as an antibacterial therapy, has declined in use as a result of the development of modern antibiotics, the cost of production of the colloidal silver compounds and the possible adverse reaction of skin discoloration. The present disclosure is of a low viscosity colloidal silver based compound which has eliminated the risk of skin discoloration and which is produced at little cost. The disclosure is of a compound in solution form, and method of application of the solution, which has ease of preparation, long term storage life, is applied by spray without the immediate need for assistance of those with extensive medical education or experience and which effects substantial antibacterial activity. The disclosed invention is in particular pertinent for use by individuals remote from sophisticated medical care in application to trauma experienced by both human and animal. The use of silver nitrate, applied by spray, is noted in Early Treatment of Burns by Open Silver Nitrate Spray, W. E. Lockhart, M.D., Rhode Island Medical Journal September 1977, pages 423–6. NLM Citation ID 78054420. The efficacy of Colloidal Silver in relation to a Colloidal Silver Complex is discussed in Antibacterial Efficacy of A Colloidal Silver Complex, Loreno Brentano, M.D., Harry Margraf, William W. Monafo, M. C., and Carl A. Moyer, M.D., F.A.C.S., Surgical Forum American College of Surgeons; volume 17, 1966 pages 76–78 (application methods are not discussed with testing limited to in vitro); Colloidal Silver, published by The Association for Advanced Colloid Research, recites research by Harry Margraf and Carl A. Moyer, M.D. relating to antiseptic compounds and colloidal silver, pages 1–40 (17, 20, 21 and 29–31). The spray delivery of highly viscous creams, such as silver sulfadiazine cream, is disclosed as an apparatus in U.S. Pat. No. 4,551,139 to Plaas. The use of silver sulfadiazine with reference to possible aerosol dispersal of wet spray of hydrophilic ointment is found in U.S. Pat. No. 3,761,590 to Fox. Helichrysum angustifolium and italicum (also referred to as immortelle and everlasting) are natural plant oils and are recognized as essential oils with properties promoting the healing process, in human and animal, of traumatic wounds including burns. Helichrysum is the distilled oil produced from flowering heads of Helichrysum Angustifolium D.C. or Italicum and is generally known for the ability to enhance human or animal wound healing and is generally accepted to have antispasmodic, analgesic, antiseptic and anti-inflammatory characteristics in relation to treatment of human or animal trauma. It is also reported to abate bleeding from wounds and in the reduction of scar tissue (The Complete Book of Essential Oils & Aroma-Therapy, pages 9, 400, Valerie Ann Worwood, published by New World Library, ISBN 0-931432-82-0; Aromatherapy Workbook, pages 16, 36, 58 and 60, published by Healing Arts Press, ISBN 0-89281-346-6; Portraits in Oils, Philippe Mailhebiau, page 65, published by Saffron Walden, ISBN 0-85207-237-6). Helichrysum is available commercially. Raw honey is known to have antiseptic qualities(A Disaster Survival Guide, Cass Ingram, D.O., page 26, published by Literary Visions Publishing, Inc., ISBN 0-911119-44-2; Scientific American, December 1996, page 102). These references are provided herewith in an Information Disclosure Statement in accordance with 37 CFR 1.97.

SUMMARY OF THE INVENTION

The present invention discloses a composition of matter comprising a therapeutically active compound with antiseptic, osmotic and other characteristics, the compound in solution, method of application of the solution, principally by a spray or mist application, and the process of preparing the solution for use in treatment of thermal burn and open wound injuries in humans and animals. Application may alternately be made by dropper or saturated bandage. Colloidal silver is combined with Helichrysum angustifolium or helichrysum italicum oil and raw honey and emulsified with water soluble lecithin by agitation. Helichrysum, a natural plant oil, is incorporated as an enhancing agent to the healing process. Raw honey provides antiseptic qualities and retards the loss of fluids from the trauma site. Water soluble lecithin is used as an emulsifier. The preferred embodiment of the compound is the combination of colloidal silver, helichrysum oil and raw honey which are emulsified in water soluble lecithin by agitation and then applied to the trauma site. The compound has no toxicity rating and may be applied with any desired frequency. There a no known allergic reaction or inter-actions associated with the compound. The compound contains no ingredients requiring dispensing by prescription. The shelf-life as been observed to be greater than one year. The colloidal silver effectively eliminates bacteria, virus and fungus precluding mutation and thus resistance to future use. There may be a degree of photosensitivity for up to ½ hour following application as a result of the inclusion of helichrysum.

The preferred embodiment method of application of the compound to thermal burns or open wounds in humans and animals is by spray or mist via a spray bottle. Application may be made by other means, such as by dropper, but is deemed to be less effective in insuring coverage of the trauma site in its entirety. Wound debriding in not indicated with the exception of removal of obvious foreign contamination. Application is preferred to be made without use of bandages which is an additional feature of the preferred spray application of the compound. Tenting is anticipated to be the preferred method of enclosure where the trauma site is to be covered, as during sleep, during the healing process.

An object of the disclosed compound is the sterilization of the trauma area and area immediately surrounding the burn or wound. An additional object is the use of a simple and effective means of delivery of the compound to the trauma site. Another objective is the application of an antibacterial agent which causes little or no pain in association with the application. An additional object of the disclosure is a simple process of preparation of the solution. A primary feature of the invention is the ability to have an antiseptic therapeutic solution with a long shelf life in areas remote from sophisticated medical assistance which may be applied to traumatic injuries in the absence of individuals with experience in medicine or chemistry. The shelf life of the disclosed solution is contrasted with the short shelf life of silver nitrate solutions rendering such solutions less useful in regions remote from medical care. An additional object is the antiseptic qualities of the disclosure in the solution as disclosed. The above indicated characteristics, ascribed to the compound, have been observed in connection with the healing of injuries where applications have been made.

BRIEF DESCRIPTION OF THE DRAWINGS

The foregoing and other features and advantages of the present invention will become more readily appreciated as the same become better understood by reference to the following detailed description of the preferred embodiment of the invention when taken in conjunction with the accompanying drawings, wherein.

DETAILED DESCRIPTION

Figure 1:
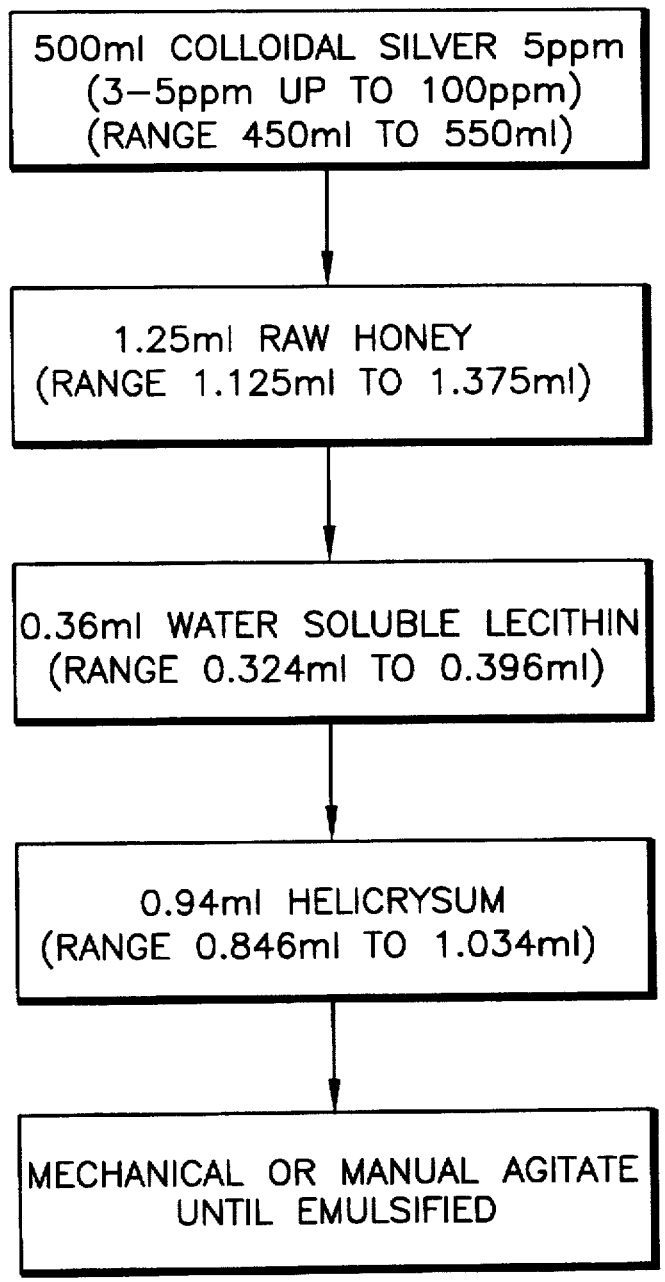
FIG. 1 is a flow diagram showing the combination of colloidal silver, helichrysum, and raw honey emulsified in water soluble lecithin demonstrating the proportions of each component and the steps in the process of preparing the solution.

The preferred embodiment of the disclosed colloidal silver compound solution, depicted in FIG. 1, is formed by the combination of 500 ml colloidal silver 5 ppm, 0.94 ml helichrysum angustifolium or italicum oil, 1.25 ml raw honey and 0.36 ml water dispersible lecithin. Colloidal silver, helichrysum oil, raw honey and water dispersible lecithin comprise the components of the invention. The ranges of volume for each of the components is plus or minus 10% of the quantities above stated. The concentration and silver particle size in colloidal silver, for therapeutic purposes, is optimum at 3–5 ppm but may be up to 100 ppm with optimum particle size between 0.005–0.015 microns but may be up to 0.2 microns. The components of colloidal silver, Helichrysum oil, and raw honey are emulsified as follows: the colloidal silver solution is poured into a container having a cover, cap or lid which will prevent spillage during agitation. Raw honey and water soluble lecithin is added. This combination is agitated until the honey is dissolved. The Helichrysum is added and the mixture is agitated until emulsification and suspension of particles is observable. The ambient temperature of the materials, prior to mixing, is such that allows the raw honey to dissolve and the mixture to emulsify. Temperatures between 40 degrees F and 95 degrees F are contemplated. Colloidal silver, helichrysum, raw honey and water dispersible lecithin are each available commercially. The colloidal silver is either obtained from a drug or chemical supplier or health food store in the parts silver per million per unit as specified. The Helichrysum used in the preparation of the solution herein was labeled 100% pure H.E.b.b.d. essential oil. The raw honey, as referred to herein, is the natural product of honey bees, is a natural osmotic, is available in most grocery stores and may be obtained from any source of nectar. The water soluble lecithin is distinguished from food grade lecithin generally available at grocery stores. The water soluble lecithin required herein is an emulsifier which is commonly available commercially via the cosmetics industry. Preparation in larger quantities, for example, should commercial sales be anticipated, would require standard container means and agitation or stirring means. The agitation combines and assists emulsification placing the raw honey and helichrysum in suspension in the colloidal silver.

The preferred application of the solution to the trauma site is by spray. The spray device may be as simple as a spray bottle available commercially at drug and chemical suppliers and at grocery stores and supermarkets. The spray application assures coverage of the trauma site in its entirety. Application may as well be made by mist, dropper, saturated bandage or direct pouring of the solution over the trauma site.

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

I claim:

1. A composition of matter comprising
   a combination of colloidal silver, raw honey and helichrysum oil emulsified with an emulsifer to form a solution.

2. The composition according to claim 1 wherein
   the emulsifier is water soluble lecithin.

3. The composition according to claim 2 wherein
   the colloidal silver is 3 to 100 ppm with a silver particle size of 0.005 to 0.2 microns; the helichrysum oil is 100% pure H.E.b.b.d. essential oil, and wherein
   the composition of matter comprises 450 ml to 550 ml colloidal silver, 0.846 ml to 1.034 ml helichrysum oil, 1.125 ml to 1.375 ml raw honey and 0.324 ml to 0.396 ml water soluble lecithin.

4. The composition according to claim 3 wherein the colloidal silver 6 to 100 ppm with a silver particle size of 0.005 to 0.015 microns.

5. The composition according to claim 4 wherein
   the combination comprises 500 ml colloidal silver to provide 6 ppm colloidal silver, 0.94 ml helichrysum oil, 1.25 ml raw honey and 0.35 ml water dispersible lecithin.

6. A method of preparing the composition according to claim 3 comprising
   pouring the colloidal silver into a container having a cover,
   adding the raw honey and the water soluble lecithin and agitating the resultant mixture until the honey is dissolved,
   adding the helichrysum oil, and
   agitating the combination of colloidal silver, raw honey and helichrysum oil until emulsification and suspension of particle is observed and the solution is formed.

7. A method for applying the composition according to claim 1 comprising the step of
   applying the solution to a trauma site in a human or animal.

8. A method for applying the composition according to claim 3 comprising the step of
   applying the solution to a trauma site in a human or animal.

9. A method for applying the composition according to claim 4 comprising the step of applying the solution to a trauma site in a human or animal.

10. The method according to claim 8 wherein the solution is applied as a spray.

11. The method according to claim 8 wherein the solution is applied as a mist.

12. The method according to claim 8 wherein the solution is applied by a dropper.

13. The method according to claim 8 wherein the solution is applied in a saturated bandage.

* * * * *